(12) United States Patent
Rmaile et al.

(10) Patent No.: US 12,734,023 B2
(45) Date of Patent: Sep. 15, 2026

(54) METHODS AND SYSTEMS FOR DYNAMICALLY ADJUSTING AN ORAL CARE ROUTINE BASED ON INTERPROXIMAL SPACE

(71) Applicant: KONINKLIJKE PHILIPS N.V., Eindhoven (NL)

(72) Inventors: Amir Hussein Rmaile, Eindhoven (NL); Steven Charles Deane, Cambridge (GB); Nigel David Young, Meadvale (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1291 days.

(21) Appl. No.: 16/625,251

(22) PCT Filed: Jun. 14, 2018

(86) PCT No.: PCT/EP2018/065739

§ 371 (c)(1),
(2) Date: Dec. 20, 2019

(87) PCT Pub. No.: WO2018/234129

PCT Pub. Date: Dec. 27, 2018

(65) Prior Publication Data

US 2020/0146435 A1 May 14, 2020

Related U.S. Application Data

(60) Provisional application No. 62/522,738, filed on Jun. 21, 2017.

(51) Int. Cl.

| | |
|---|---|
| ***A61C 17/02*** | (2006.01) |
| ***A61B 5/00*** | (2006.01) |
| ***A61C 17/22*** | (2006.01) |

(52) U.S. Cl.

CPC ............ *A61C 17/02* (2013.01); *A61B 5/4547* (2013.01); *A61C 17/0202* (2013.01); *A61C 17/221* (2013.01)

(58) Field of Classification Search

CPC .............. A61C 17/005; A61C 17/0211; A61C 17/0217; A61C 17/028; A61C 17/16;

(Continued)

(56) References Cited

U.S. PATENT DOCUMENTS

| | | |
|---|---|---|
| 4,795,347 A | 1/1989 | Maurer |
| 6,241,519 B1 | 6/2001 | Sedelmayer |

(Continued)

FOREIGN PATENT DOCUMENTS

| | | |
|---|---|---|
| CN | 101569535 A | 11/2009 |
| JP | H0947323 A | 2/1997 |

(Continued)

OTHER PUBLICATIONS

International Search Report and Written Opinion, International Application PCT/EP2018/065739, Mailed on Sep. 14, 2018.

*Primary Examiner* — Eric J Rosen
*Assistant Examiner* — Sydney J Pulvidente

(57) ABSTRACT

A method (800) for adjusting a user's oral care routine by an oral care device (10) based on interproximal spacing, the method including the steps of: (i) obtaining (820), using the oral care device, information about an interproximal space (66) in the user's mouth; and (ii) automatically adjusting (850), based on the obtained information, a parameter of the oral care device, wherein the dynamic adjustment is configured to improve oral care of the interproximal space.

14 Claims, 6 Drawing Sheets

(58) Field of Classification Search
CPC ..... A61C 17/20; A61C 19/04; A61C 17/0202; A61C 17/221; A61C 17/28; A61C 17/3454; A61C 15/00–048; A61C 9/004–0086
See application file for complete search history.

(56) References Cited

U.S. PATENT DOCUMENTS

| | | | | |
|---|---|---|---|---|
| 6,766,549 | B2 | 7/2004 | Klupt | |
| 9,144,476 | B2 | 9/2015 | Iwahori | |
| 9,565,927 | B2 | 2/2017 | Bloch | |
| 2014/0308625 | A1* | 10/2014 | Fairley | A61C 19/066<br>433/217.1 |
| 2016/0331117 | A1* | 11/2016 | Follows | A61C 17/221 |
| 2017/0086954 | A1 | 3/2017 | De Jager et al. | |
| 2017/0095261 | A1* | 4/2017 | Strbac | A61B 17/1626 |
| 2018/0221124 | A1* | 8/2018 | Carlyle | A61C 15/00 |

FOREIGN PATENT DOCUMENTS

| | | | |
|---|---|---|---|
| WO | 2016074705 | A1 | 5/2016 |
| WO | 2016156098 | A1 | 10/2016 |

* cited by examiner

METHODS AND SYSTEMS FOR DYNAMICALLY ADJUSTING AN ORAL CARE ROUTINE BASED ON INTERPROXIMAL SPACE

This application is the U.S. National Phase application under 35 U.S.C. § 371 of International Application No. PCT/EP2018/065739, filed on 14 Jun. 2018, which claims the benefit of U.S. Provisional Application No. 62/522,738, filed 21 Jun. 2017. These applications are hereby incorporated by reference herein.

FIELD OF THE INVENTION

The present disclosure relates generally to systems and methods for determining the size of interproximal space and dynamically adjusting an oral care routine accordingly.

BACKGROUND

To facilitate proper oral cavity health, it is important to ensure that there is adequate cleaning of all dental surfaces, including the interproximal space between teeth. Research has shown that improper cleaning of interproximal spaces leads to gum and periodontal disease, and can lead to caries.

Dental practitioners typically recommend that their patients clean between the teeth using various interdental cleaning methods or devices such as floss, an interdental brush, or a water jet, among other methods. Dental floss, for example, is often recommended for individuals with narrow interdental spaces, and interproximal brushes have been recommended for periodontal patients or for patients with open embrasures.

One major issue with cleaning these interproximal spaces is that every person has different anatomy and morphology of the teeth, thereby creating different sizes, shapes, and forms of the interproximal spaces. There are different interproximal spaces even within the mouth of a single person. To address variations in interproximal spacing, many dental practitioners measure the spacing and prescribe interproximal cleaning aids with different sizes for different sites in the patient's mouth. For example, a 0.6 mm diameter interproximal brush may be utilized for a first site, a 0.9 mm diameter interproximal brush may be utilized for a second site, and a 1.1 mm diameter interproximal brush may be utilized for a third site.

These traditional approaches to cleaning interproximal spaces are onerous. Patients often struggle to follow the dental practitioner's instructions properly, and often forget which interproximal brush to use at which location within the mouth. And for patients that are able to follow the dental practitioner's instructions properly, they tend to quit after few days or few weeks as motivation fades away.

Accordingly, there is a continued need in the art for methods and systems for oral care devices that dynamically adjust an oral care routine based on measurements of the user's interproximal space.

SUMMARY OF THE INVENTION

The present disclosure is directed to inventive systems and methods for determining the size of interproximal space and dynamically adjusting an oral care routine accordingly. Various embodiments and implementations herein are directed to an oral care device that utilizes information about interproximal spacing to automatically and dynamically modify an oral care routine, thereby cleaning interproximal spaces comprising a plurality of sizes and shapes using a single device. The oral care device can include a system for measuring interproximal spaces, and/or it can receive information about interproximal spacing from a separate component such as a scanner, smartphone, or other mechanism. Based on the received information about interproximal spacing, the oral care device automatically adjusts the oral care routine to improve cleaning of each interproximal space. Adjustments to the oral care routine may include, for example, adjusting a spray pattern and/or intensity, among other options.

Generally in one aspect, a method for adjusting a user's oral care routine by an oral care device based on interproximal spacing is provided. The method includes the steps of: (i) obtaining, using the oral care device, information about an interproximal space in the user's mouth; and (ii) automatically adjusting, based on the obtained information, a parameter of the oral care device, wherein the dynamic adjustment is configured to improve oral care of the interproximal space.

According to an embodiment, the obtaining step comprises a mechanical measurement of the interproximal space.

According to an embodiment, the oral care device comprises a sensor configured to obtain the information about the interproximal space.

According to an embodiment, the obtaining step comprises receiving, by the oral care device, information about an interproximal space in the user's mouth.

According to an embodiment, the parameter comprises a number of cleaning shots emitted from the oral care device.

According to an embodiment, the parameter comprises a width of an air and liquid spray emitted from the oral care device.

According to an embodiment, the oral care device comprises a biased mechanical element configured to respond to an interproximal space.

According to an aspect, a method for adjusting a user's oral care routine by an oral care device based on interproximal spacing is provided. The method includes the steps of: (i) obtaining, using the oral care device, information about an interproximal space in the user's mouth; (ii) analyzing, by a controller of the oral care device, the obtained information about an interproximal space in the user's mouth; (iii) automatically adjusting, based on the analysis, a parameter of the oral care device, wherein the dynamic adjustment is configured to improve oral care of the interproximal space; and (iv) executing, using the automatically adjusted parameter, an oral care routine.

According to an aspect is an oral care device configured to automatically and dynamically adjust a cleaning parameter of the oral care device based on interproximal spacing in a user's mouth. The device includes a sensing and actuation mechanism configured to: obtain information about an interproximal space in the user's mouth; and automatically adjust, based on the obtained information, a parameter of the oral care device, wherein the dynamic adjustment is configured to improve oral care of the interproximal space.

According to an embodiment, the device further includes a controller configured to analyze the obtained information about an interproximal space in the user's mouth, wherein said automatic adjustment is based at least in part on the analysis.

According to an embodiment, the sensing and actuation mechanism comprises a mechanical element configured to directly measure the interproximal space. According to an embodiment, the sensing and actuation mechanism comprises a sensor configured to obtain the information about the interproximal space.

As used herein for purposes of the present disclosure, the term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of an oral care device configured to automatically and dynamically adjust an oral care routine. More generally, Applicant has recognized and appreciated that it would be beneficial to provide a device that adjusts one or more parameters of an oral care routine for an interproximal space, based on a measurement of that interproximal space. Accordingly, the methods and systems described or otherwise envisioned herein provide an oral care device that utilizes information about interproximal spacing to automatically and dynamically modify an oral care routine, thereby cleaning interproximal spaces comprising a plurality of sizes, shapes, and forms using a single device. According to an embodiment, the oral care device obtains information about an interproximal space using a mechanical and/or digital measurement. According to another embodiment, the oral care device receives measurement information from another source. The oral care device utilizes the obtained or received information to adjust the cleaning session, thereby improving cleaning of interproximal spaces.

The embodiments and implementations disclosed or otherwise envisioned herein can be utilized with any oral care device. Examples of suitable oral care devices include an oral irrigator, a toothbrush, or other oral care device. However, the disclosure is not limited to these enumerated devices, and thus the disclosure and embodiments disclosed herein can encompass any oral care device.

Figure 1:
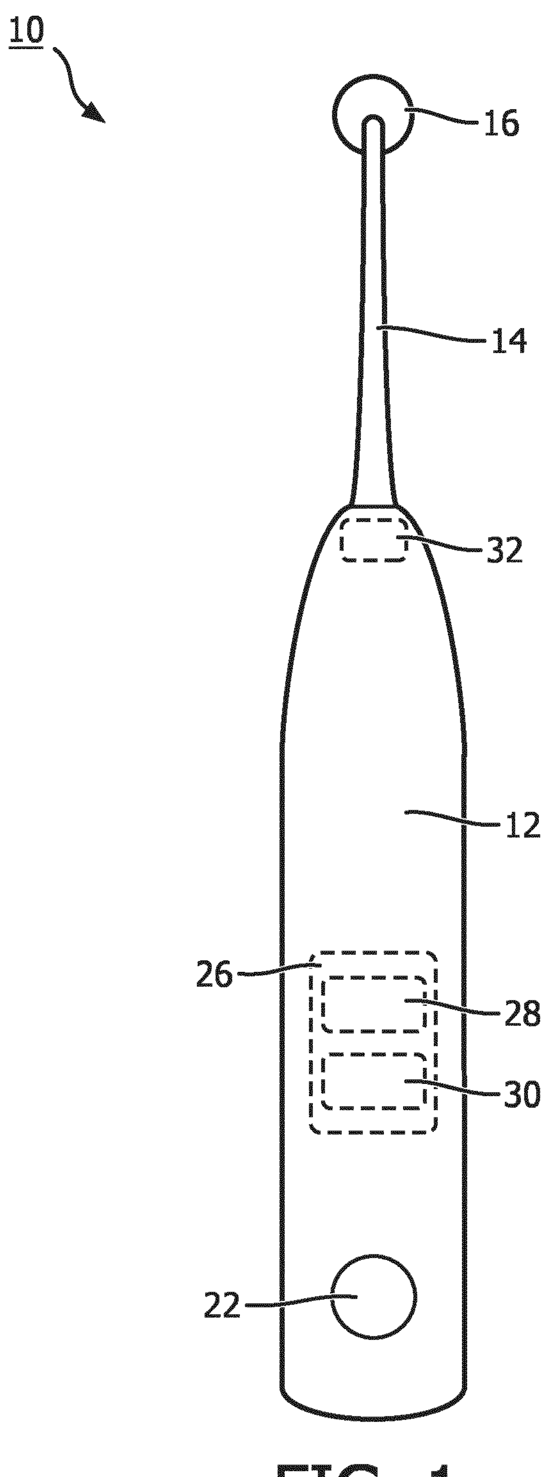
FIG. 1 is a schematic representation of an oral care device, in accordance with an embodiment.

Referring to FIG. 1, in one embodiment, is an oral care device 10 used to clean the interproximal spaces between teeth. Oral care device 10 includes a handle or body portion 12 designed to be held in a user's hand, and an oral care implement 14. Oral care implement 14 may have a curved portion at the distal end thereof, to assist in convenient positioning of the oral care implement in the mouth by the user. The oral care implement may have a function head 16 at the distal end thereof.

Oral care device 10 may also include a user interface 22 used to turn the device on or off or implement operation, and may provide for communication with the user. Oral care device 10 also includes a controller 26, which is part of control system 100 shown in FIG. 2. Controller 26 may be formed of one or multiple modules, and is configured to operate the oral care device 10 in response to an input. Controller 26 can comprise, for example, a processor 28 and a memory 30. According to an embodiment, an operating system may contain code which, when executed by controller 26, controls operation of the hardware components of oral care device 10.

According to an embodiment, oral care device 10 can optionally include one or more sensors 32. Sensor 32 is shown in FIG. 1 within body portion 12, but may be located anywhere within the device, including for example within oral care implement 14 or function head 16. According to one embodiment, sensor 32 can be integral to controller 26. Sensor 32 can comprise, for example, an inertial motion sensor such as an accelerometer, gyroscope, or magnetic sensor. According to an embodiment, sensor 32 is configured to provide readings of six axes of relative motion (three axes translation and three axes rotation), using for example a 3-axis gyroscope and a 3-axis accelerometer. As another example, sensor 32 is configured to provide the readings of nine axes of relative motion using, for example, 3-axis gyroscope, a 3-axis accelerometer, and a 3-axis magnetometer. Other sensors may be utilized either alone or in conjunction with these sensors, including but not limited to a pressure sensor and other types of sensors, such as a capacitive sensor, a camera, a photocell, a clock, a timer, and other types of sensors. Many different types of sensors could be utilized, as described or otherwise envisioned herein. According to an embodiment, sensor 32 is configured to generate information indicative of the acceleration and angular orientation of oral care device 10. The sensor may comprise two or more sensors 32 that function together as the 6-axis or a 9-axis spatial sensor system.

Figure 2:
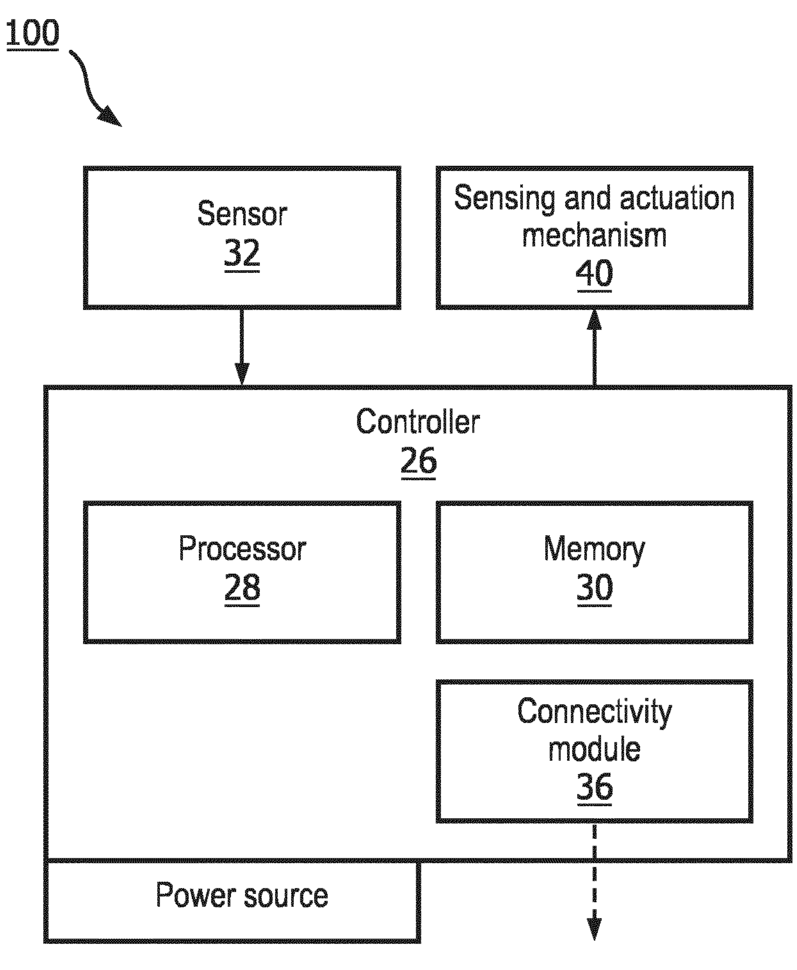
FIG. 2 is a schematic representation of a control system of an oral care device, in accordance with an embodiment.

Referring to FIG. 2, in one embodiment, is a schematic representation of a control system 100 of oral care device 10. Control system 100 comprises controller 26 with a processor 28 and a memory 30, which can store an operating system as well as sensor data. The system may also comprise a power source. Control system 100 can optionally include a user interface 22, as shown in FIG. 1, which is configured to transmit or receive information to the user. An optional sensor 32 of the system, which may be an inertial motion sensor such as an accelerometer, gyroscope, or magnetic sensor, generates sensor data in response to motion and communicates that data to controller 26.

A connectivity module 36 of the device can be configured and/or programmed to receive and/or transmit data from or to a wireless transceiver (not shown). For example, connectivity module 36 may transmit sensor data via a Wi-Fi connection over the internet or an intranet to a dental professional, a database, or other location. Alternatively, connectivity module 36 may receive and/or transmit sensor or feedback data via a Bluetooth or other wireless connection from or to a local device (e.g., a separate computing device), database, or other transceiver. For example, connectivity module 36 allows the user to transmit sensor data to a separate database to be saved for long-term storage, to transmit sensor data for further analysis, to transmit user feedback to a separate user interface, or to share data with a dental professional, among other uses. Connectivity module 36 may also be a transceiver that can receive user input information, such as interproximal spacing information. Other communication and control signals described herein can be effectuated by a hard wire (non-wireless) connection, or by a combination of wireless and non-wireless connections.

According to an embodiment, control system 100 of oral care device 10 can be programmed and/or configured to automatically and dynamically adjust an oral care routine via a sensing and actuation mechanism 40, based on interproximal spacing. For example, as disclosed or otherwise envisioned herein, oral care device 10 can modify an output of the function head 16 or other component of the oral care device in order to adapt to a specific interproximal space and improve cleaning of that space. According to another embodiment, oral care device 10 can modify a physical structure of the oral care implement itself to adapt to a specific interproximal space and improve cleaning of that space. According to yet another embodiment, oral care device 10 may adjust an output to adapt to a specific interproximal space, such as providing a larger or smaller amount of cleaning liquid ejected from the oral care device into the interproximal space during a certain timeframe, among other variations in output. For example, the system may increase the volume of liquid delivered by the device for larger interproximal spaces, and reduce the volume of liquid delivered by the device for smaller interproximal spaces. Many other embodiments of a dynamic sensing and actuation mechanism 40 are possible.

Sensing and actuation mechanism 40 can receive input from a sensor 32 of the oral care device 10, which can directly or indirectly measure interproximal space. Sensor 32 can be any of the sensors described or otherwise envisioned herein, and can be programmed and/or configured to obtain sensor data regarding one or more of the user's interproximal spaces before, during, and/or after a cleaning session. Controller 26 can receive the sensor data from sensor 32 in real-time or periodically. For example, sensor 32 may send a constant stream of sensor data to controller 26 for storage and/or analysis, or may temporarily store and aggregate or process data prior to sending it to controller 26. Once received by controller 26, the sensor data can be processed by processor 28 and the processor can direct the adjustment of the oral care routine accordingly.

Alternatively or in conjunction with this process, sensing and actuation mechanism 40 can receive input from an external sensor or information source containing information about interproximal space. For example, measurements of interproximal space may be obtained by the user or a dental professional at a previous time, and that information can be provided to the oral care device. The feedback mechanism receives that information and uses it to dynamically adjust the output of the device for one or more measured interproximal locations.

Figure 3:
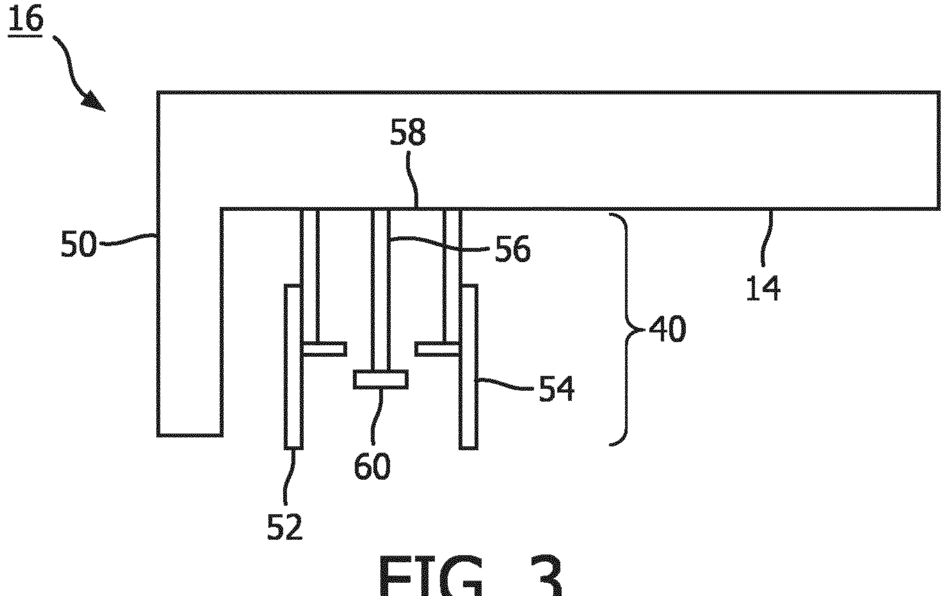
FIG. 3 is a schematic representation of a function head of an oral care device, in accordance with an embodiment.

Referring to FIG. 3, in one embodiment, is a function head 16 configured to determine the size of an interproximal space and dynamically adjust oral care accordingly. The function head is positioned at or near the end of oral care implement 14, which extends outwardly from the body portion 12 of oral care device 10.

According to this embodiment, the function head 16 comprises a spacer 50 which is configured to assist the user with proper positioning of the oral care device relative to the teeth. The spacer can be a rigid material, or it can comprise or include a softer material. For example spacer 50 could be a rigid plastic, or it could be a rubberized or other soft plastic or polymer component extending from the function head in the direction of the user's teeth when the oral care device is positioned within the mouth. When spacer 50 touches against or rubs against the user's teeth, the sensing or measuring mechanism is more properly aligned with the teeth and able to obtain one or more measurements of the interproximal space. Additionally, spacer 50 can provide the optimal space between the function head outlet 58 and the teeth in order to provide improved efficacy of the oral care session.

The function head further comprises an automated sensing and actuation mechanism 40 composed of a fixed inner part 56 and two movable outer parts 52 and 54 positioned on either side of the fixed inner part, all of which extend outwardly from function head 16 in the direction of the user's teeth when the oral care device is positioned within the user's mouth. The automated sensing and actuation mechanism 40 can directly or indirectly measure the interproximal space and can automatically respond to that measurement to change a parameter of the oral care device operation, such as increasing velocity or amount of liquid output or the speed of operation, among many other changes. Referring to FIG. 3, one or both of outer parts 52 and 54 are movable along the function head 16 and can be biased away from fixed inner part 56, such as with a spring or other bias. In the default position, the outer part 54 is biased away from inner part 56 and there is a maximum distance between moveable outer part 54 and fixed inner part 56. As the tip or end of moveable outer part 54 is pushed against the teeth and at least partially into an interproximal space, outer part 54 is pushed toward the inner part 56 against its bias, and the distance between the inner part 56 and outer part 54 is decreased. In this way, the automated sensing and actuation mechanism obtains a mechanical measurement of the interproximal space and can automatically and dynamically respond.

According to an embodiment, fixed inner part 56 comprises a head portion 60. Accordingly, as outer part 54 is pushed by a tooth against its bias, thereby decreasing the distance between the outer part 54 and the fixed inner part 56, the area around head portion 60 decreases. So, for example, if the oral care device is dispensing fluid, such as the device shown in FIGS. 3-5, the cleaning jet or flow narrows for a narrower interproximal space. When the automated sensing and actuation mechanism 40 encounters a wider interproximal space, the outer part 52 and/or 54 is allowed to move with its bias and the area around head portion 60 increases and the cleaning jet or flow widens for this wider interproximal space.

According to an embodiment, outer parts 52 and/or 54 can be electronically controlled by the oral care device rather than mechanically controlled. For example, outer part 52 and/or 54 can be moved by an actuator located at least partially within oral care implement 14 and/or function head 16. The actuator can respond to interproximal space measurements that the device receives or obtains directly, such as with a camera as described or otherwise envisioned herein.

Figure 4:
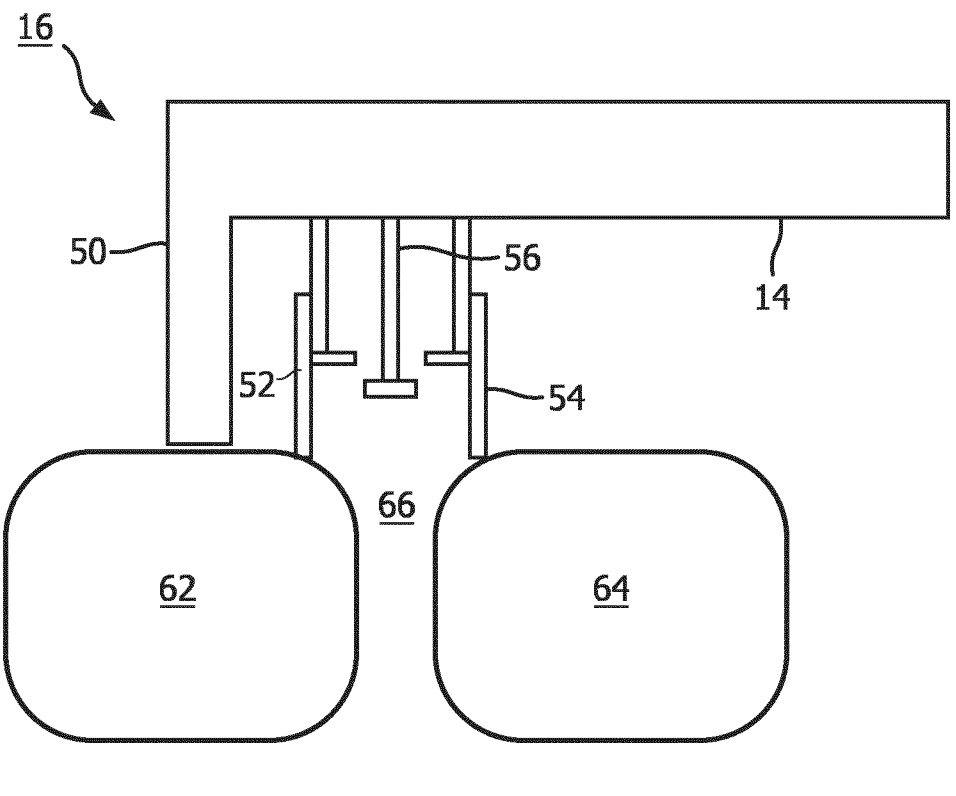
FIG. 4 is a schematic representation of a function head of an oral care device, in accordance with an embodiment.

Referring to FIG. 4 is an embodiment of the function head 16 relative to two teeth 62 and 64, which form an interproximal space 66 between them. Interproximal space 66 in this embodiment is a larger space, and therefore outer parts 52 and/or 54 are biased out from fixed inner part 56 and the cleaning jet or flow is wider and/or faster for this wider interproximal space. In an embodiment in which the positioning of outer parts 52 and/or 54 is controlled by an actuator, the device obtains or receives information about the spacing 66 and moves outer parts 52 and/or 54 to a wider configuration.

Figure 5:
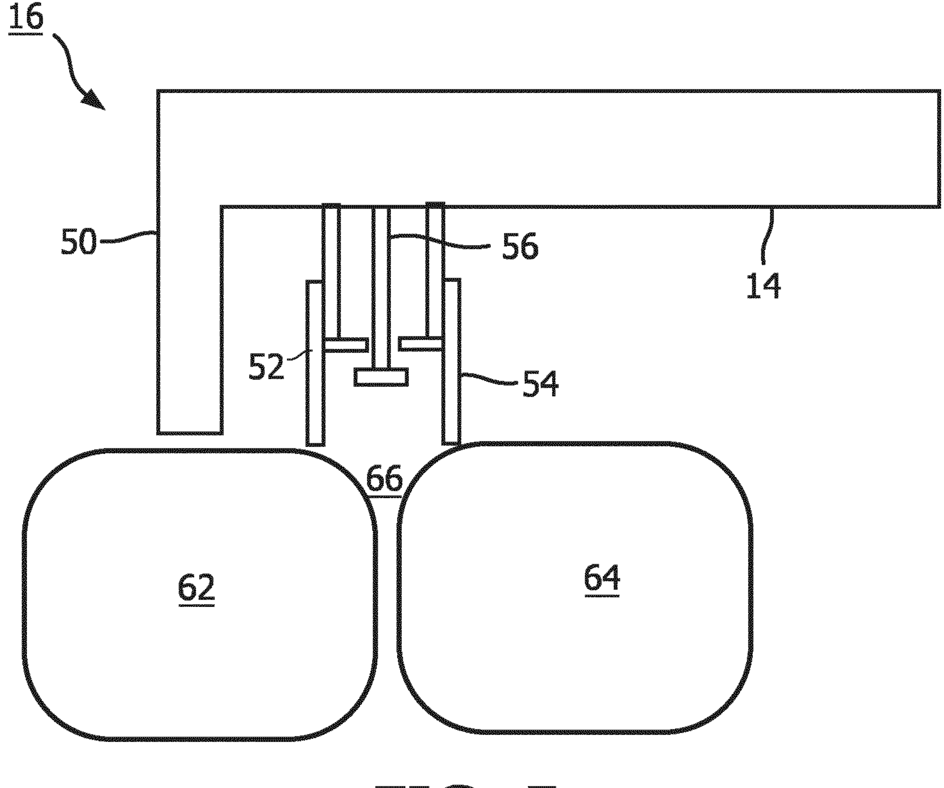
FIG. 5 is a schematic representation of a function head of an oral care device, in accordance with an embodiment.

In contrast, referring to FIG. 5 is an embodiment of the function head 16 relative to two teeth 62 and 64, which form an interproximal space 66. Interproximal space 66 in this embodiment is a smaller space than the interproximal space shown in FIG. 4, and therefore outer parts 52 and/or 54 are pushed against their bias and toward fixed inner part 56, and the cleaning jet or flow is narrower and/or slower for this narrower interproximal space. In an embodiment in which the positioning of outer parts 52 and/or 54 is controlled by an actuator, the device obtains or receives information about the spacing 66 and moves outer parts 52 and/or 54 to a narrower configuration.

In addition to pushing outer parts 52 and/or 54 against their bias and toward fixed inner part 56, one or more of outer parts 52 and 54 can move in other planes relative to the fixed inner part. For example, one or more of outer parts 52 and 54 can be pushed inward toward oral care implement 14 due to interaction with a tooth surface, and the cleaning jet or flow will be wider and/or faster for an interproximal space. Similarly, when outer parts 52 and/or 54 are not interacting with a tooth surface, or are interacting with a smaller interproximal space, the outer parts will be closer toward the fixed inner part 56, thereby reducing the cleaning jet or flow.

One benefit of the embodiment depicted in FIGS. 4 and 5 is that a single function head 16 is utilized for a variety of interproximal spaces, and can automatically and dynamically respond to those different interproximal spaces without requiring more than one function head. Accordingly, the user can clean all or most interproximal spaces without multiple oral care implements, function heads, or other manual adjustments of the oral care device.

Figure 6A:
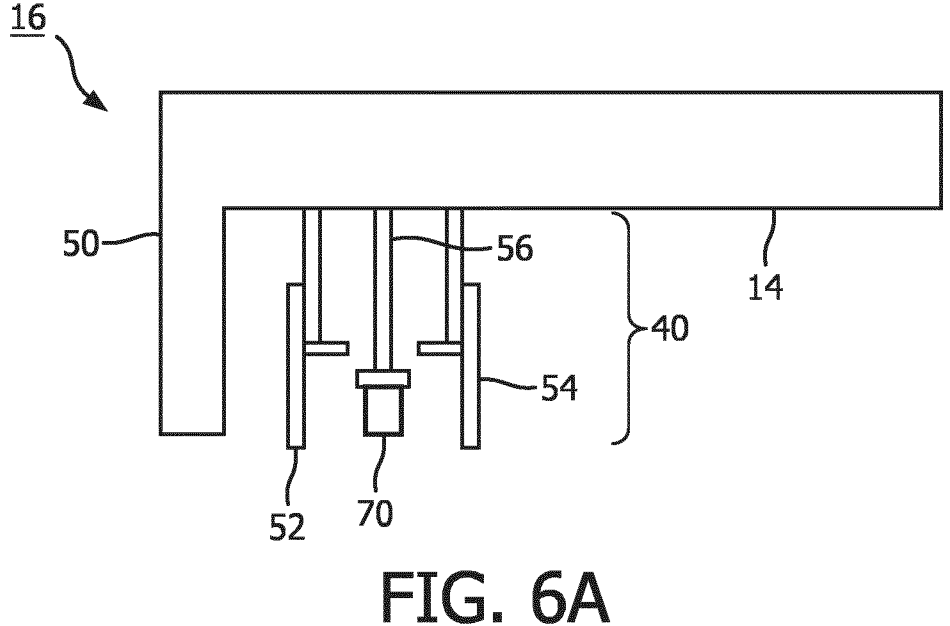
FIG. 6A is a schematic representation of a function head of an oral care device, in accordance with an embodiment.

Referring to FIG. 6A, in one embodiment, is a schematic representation of a function head 16 configured to determine the size of an interproximal space and dynamically adjust the oral care routine accordingly. The function head is positioned at or near the end of oral care implement 14, which extends outwardly from the body portion 12. A spacer 50 is configured to assist the user with proper positioning of the oral care device relative to the teeth. The automated sensing and actuation mechanism 40 is composed of a fixed inner part 56 and two movable outer parts 52 and 54 positioned on the sides of the fixed inner part, all of which extend outwardly from oral care implement 14 in the direction of the user's teeth when the device is positioned within the user's mouth. The embodiment depicted in FIG. 6A further comprises a sensor 70 such as an imaging sensor configured to obtain sensor data representative or otherwise informative of the interproximal space. For example, sensor 70 may be a camera or other imager positioned and/or configured to obtain image data of the interproximal space. The data may be actual images, or may be other imaging data representative of the interproximal space.

Figure 6B:
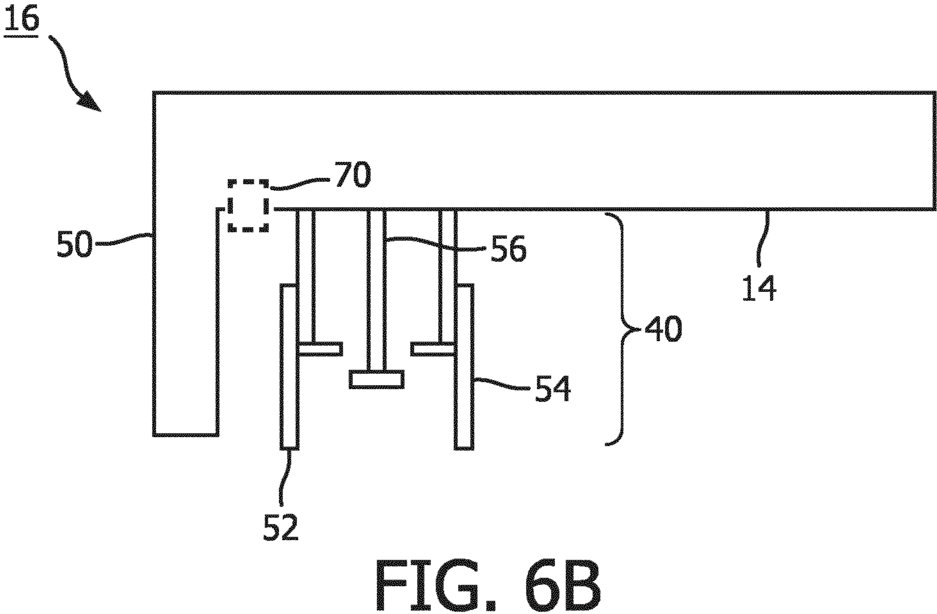
FIG. 6B is a schematic representation of a function head of an oral care device, in accordance with an embodiment.

Although sensor 70 is depicted as being affixed to head portion of the fixed inner part, the sensor may be positioned anywhere within or the function head 16. For example, referring to FIG. 6B, sensor 70 is entirely or partially embedded or positioned within the function head 16. The function head may comprise an opening or window with sensor 70 positioned behind the opening or window to provide protection to the components which are still able to obtain sensor data. Although not shown, sensor 70 may be positioned anywhere along the oral care implement where it will be capable of obtaining interproximal measurement information, including but not limited to along or in spacer 50.

Figure 7A:
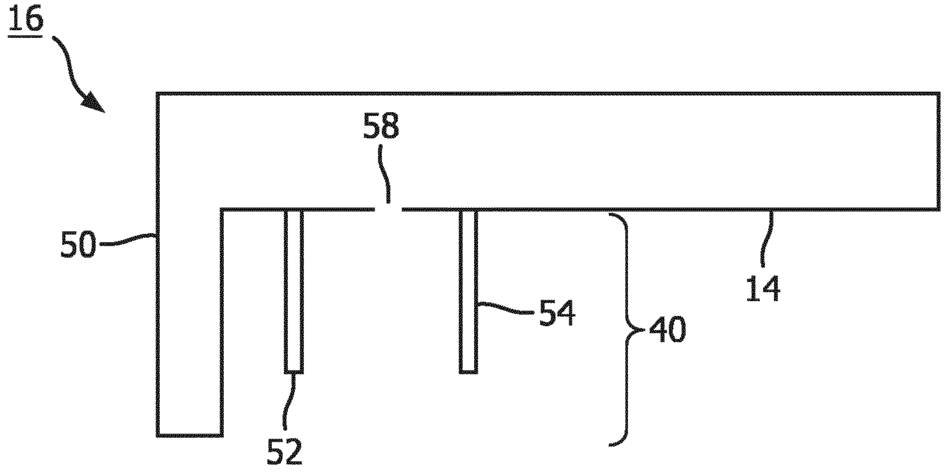
FIG. 7A is a schematic representation of a function head of an oral care device, in accordance with an embodiment.

Referring to FIG. 7A, in one embodiment, is a schematic representation of a function head 16 configured to dynamically adjust oral care. The function head is positioned at or near the end of oral care implement 14, which extends outwardly from the body portion 12 of oral care device 10. A spacer 50 is configured to assist the user with proper positioning of the oral care device relative to the teeth. The sensing and actuation mechanism 40 is composed of two outer parts 52 and 54 which are separated by a space which allows water, air, and/or any other component of a cleaning session to exit the function head outlet 58. According to an embodiment, one or both of outer parts 52 and 54 are moveable to modify the flow of the water, air, and/or other component from the oral care device. Accordingly, the function head may comprise an actuator configured to move one or both of outer parts 52 and 54 in response to interproximal spacing information.

Figure 7B:
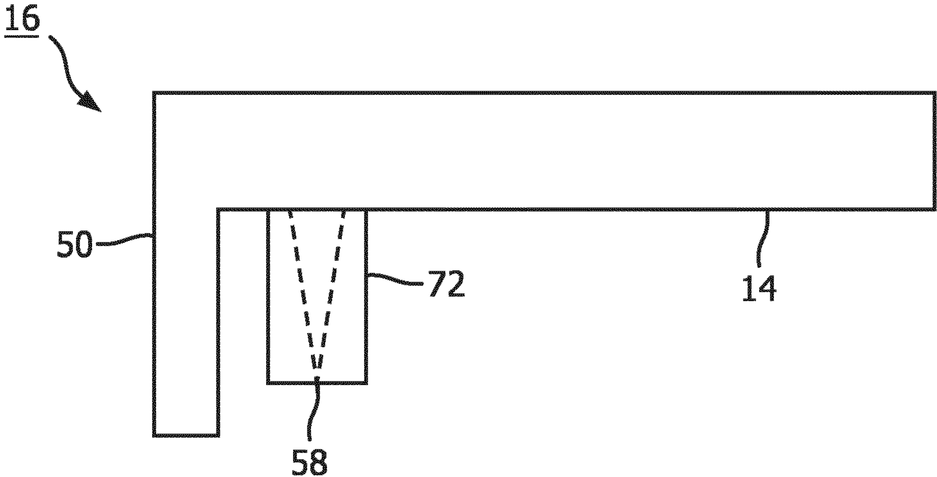
FIG. 7B is a schematic representation of a function head of an oral care device, in accordance with an embodiment.

Referring to FIG. 7B, in one embodiment, is a schematic representation of a function head 16 configured to dynamically adjust oral care. The function head 16 comprises an extension 72 comprising or defining a pathway through which water, air, and/or any other component of a cleaning session can travel to function head outlet 58. For example, the width of the outlet of pathway 72 may be adjustable to provide a wider or narrower outlet. For a device expelling water and/or air from the outlet, the wider outlet will allow more water and/or air to exit the device and impact the interproximal space, which will improve cleaning of wider spaces. A narrower outlet will allow less water and/or air to exit the device and impact the interproximal space, which will improve cleaning of narrower spaces.

Figure 8:
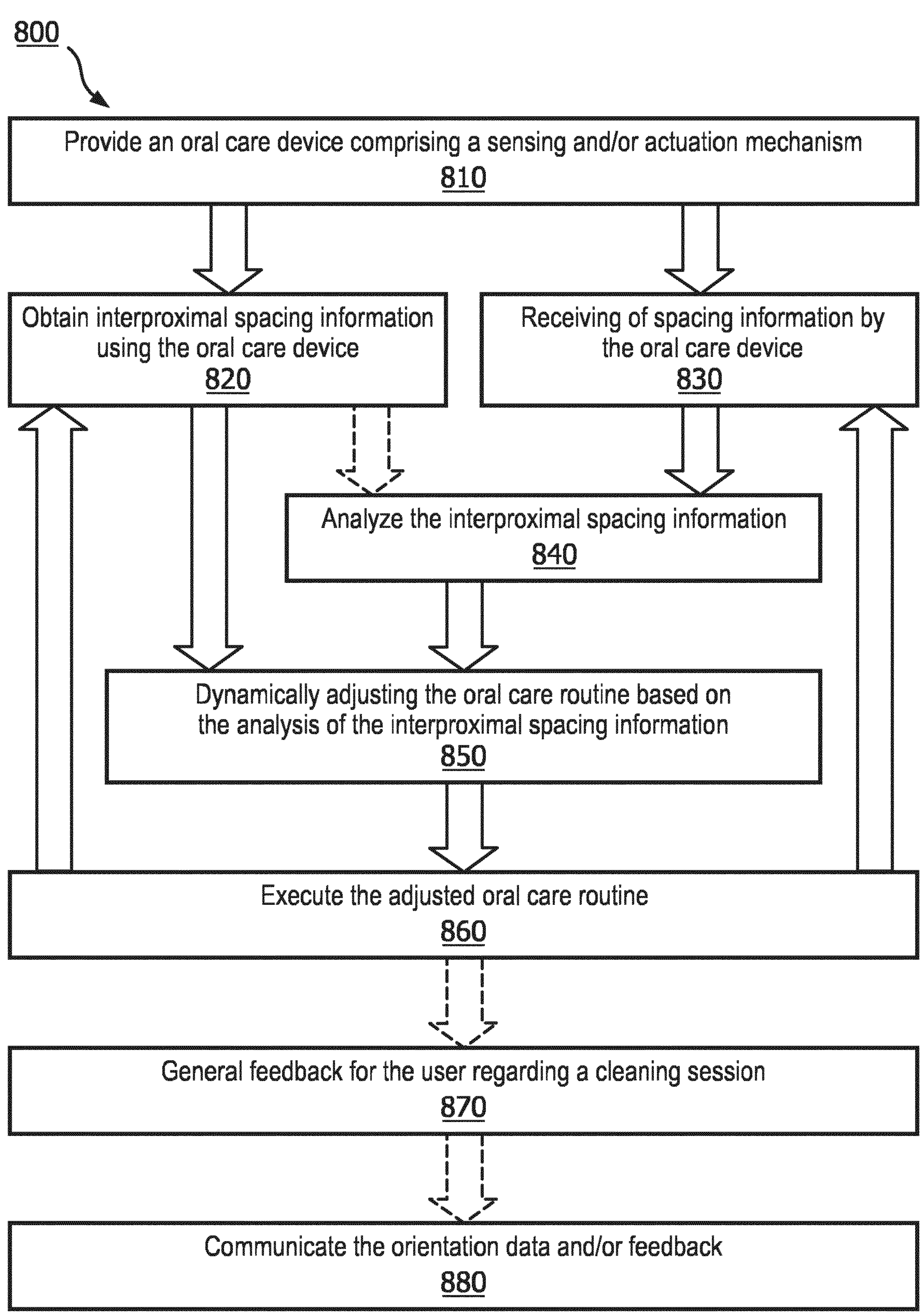
FIG. 8 is a flowchart of a method for automatically and dynamically adjusting an oral care routine, in accordance with an embodiment.

Referring to FIG. 8, in one embodiment, is a flowchart of a method 800 for dynamically adjusting an oral care routine based on interproximal spacing. At step 810 of the method, an oral care device 10 configured to obtain and/or receive interproximal spacing information is provided. Oral care device 10 can be any of the devices or embodiments described or otherwise envisioned herein. According to one embodiment, oral care device 10 comprises a handle or body 12 and an oral care implement 14 with a function head 16. The oral care device also optionally comprises a controller 26 comprising or in communication with a processor 28 and a memory 30. Function head 16 of oral care device 10 can also comprise an actuation mechanism 40 configured to dynamically adjust oral care based on interproximal spacing, and can further comprise a sensing mechanism configured to obtain or receive information about interproximal spacing.

At step 820 of the method, oral care device 10 obtains spacing information about one or more interproximal spaces within a user's mouth. According to an embodiment, oral care device 10 comprises a measurement mechanism, which may be mechanical, digital, or both, configured to obtain the spacing information. For example the oral care device may comprise a sensing mechanism such as a mechanical mechanism as described in conjunction with FIGS. 3-5, among many other mechanisms. According to another example, the oral care device may comprise a sensing mechanism such as a sensor 70 configured to obtain images or other sensor data representative of interproximal spacing information, as shown for example in the embodiments described with regard to FIGS. 6A and 6B. According to an embodiment, sensor 70 is a camera configured to obtain one or more images for one or more interproximal spaces.

According to an embodiment, there are many other mechanisms for measuring interproximal spaces. For example, interproximal spacing can be deduced by detecting the elasticity of the gums between two neighboring teeth, such as through a tension test or a vibrating probe using indentation measurements. Interproximal spacing may also be analyzed by detecting roughness (such as the stick/slip phenomenon), by measuring resistance changes in an oral care device, by looking at the response of tissues to cold or pressure stimulus, through ultrasound imaging, by temperature changes such as whether the temperature of the interproximal tissue is different from the temperature of the teeth, a blood detection sensor to detect interproximal tissues, capacitive contact forces to measure the accumulation of fluid in interproximal tissues, and/or by measuring swelling using impedance measurements, Doppler measurements, or other measurements. These are just a few ways to measure the interproximal spaces in the user's mouth.

At step 830 of the method, which may be performed together with, or instead of step 820 of the method, oral care device 10 receives spacing information about one or more interproximal spaces within a user's mouth. According to an embodiment, the oral care device receives information about spacing information from another device or another external information source. According to an embodiment, the oral care device is in communication with and receives information from a device that scans or images one or more interproximal spaces of the user's mouth, such as a smartphone, smart mirror, wearable object such as smart glasses, or an oral device other than the oral care device 10, or a dental professional. According to an embodiment, multiple images may be obtained and the image information can be stitched together to give greater coverage of the oral cavity, and thus more interproximal locations, than would be possible by using a single image.

According to an embodiment, the device scans or images the one or more interproximal spaces of the user's mouth and stores and/or transmits that information to the oral care device directly, or to a remote server or storage device that the oral care device can later access. For example, the oral care device may periodically communicate with the remote server, and/or storage device to inquire about interproximal spacing information and any other information required for the method or system.

According to an embodiment, the oral care device comprises a separate function head, or other component configured to measure interproximal spaces using a mechanical and/or digital mechanism. The separate function head or other component can obtain measurement information and store and/or transmit to the oral care device, or to a remote server or storage device that the oral care device can later access. The oral care device may store the measurement information directly, which can be accessed later by a function head configured for dynamic adaptation to interproximal spaces. The separate function head, or other component may be color-coded or otherwise modified or identified to provide differentiating information to the user.

According to an embodiment, the oral care device receives interproximal spacing information from a dental professional. Dental professionals measure interproximal gaps during appointments and can recommend different interproximal function head sizes. The dental professional can then provide that information to the user or to the user's system and that information can be utilized during subsequent cleaning sessions. This may be especially useful for orthodontists, as the user's interproximal spaces may change significantly over time due to an orthodontic treatment such as braces. It may be advantageous to have a record of the size of the interproximal space as it changes over time so that the proper tools and cleaning routine are utilized.

At optional step 840, the system analyzes the obtained and/or received interproximal spacing information. For example, according to an embodiment, a sensing mechanism such as a sensor 70 which is configured to obtain images or other sensor data representative of interproximal spacing information is in communication with the controller 26. The controller comprises or is in communication with processor

28, which can perform one or more functions of the method. The controller analyzes the obtained and/or received interproximal spacing information to determine an interproximal space, which allows the system to determine, develop or otherwise identify an appropriate response by the oral care device to that interproximal space. For example, as described or otherwise envisioned herein, the oral care device can modify an output based on interproximal space, and the controller can direct the modification of the output based on the analysis of the obtained and/or received interproximal spacing information. As just one example, the controller may be configured, programmed, or otherwise designed to adapt the output to a certain width, velocity, or other parameter when a certain interproximal spacing is identified.

According to an embodiment, the system analyzes the obtained or received information and determines the interproximal distance or spacing by, for example, measuring the distance between the two teeth, which might be recognized as two white objects. The interproximal distance or spacing may also be determined by measuring the width of the gingiva, which might be recognized as a pink or red color. The interproximal distance or spacing may also be determined by measuring the base of a black triangle, or a region of missing gums between teeth.

At step 850 of the method, oral care device 10 dynamically and automatically adjusts the oral care routine based on the obtained or received interproximal spacing. According to an embodiment, the controller directs the function head of the oral care device to dynamically and automatically adjust the oral care routine based on the analysis of the obtained or received interproximal spacing. For example, as described with regard to FIGS. 6A and 6B, the oral care device may comprise a sensing mechanism such as a sensor 70 configured to obtain images or other sensor data representative of interproximal spacing information. The controller analyzes that information and provides the analysis or an instruction to the function head 16 to adapt the oral care output based on the interproximal space. According to another embodiment, such as that described with regard to FIGS. 3-5, oral care device 10 comprises a measurement mechanism and automatically and dynamically adapts the oral care output to each interproximal space.

According to another embodiment, function head 16 of oral care device 10 comprises two components each having a different function/output. The output that may be different is velocity, spray angle or direction, air/liquid mix, and other parameters. During use, the oral care device obtains or otherwise determines interproximal spacing, and can automatically preferably use one or both components depending on the interproximal space. Alternatively, the oral care device may tell the user to actuate a different component of the function head. According to yet another embodiment, the oral care device may comprise multiple function heads each configured to preferably clean interproximal spaces of a certain size or range, and the system may direct the user to utilize specific function heads in specific locations of the mouth.

According to another embodiment, oral care device 10 modifies the cleaning routine of a different device. For example, the oral care device determines or obtains interproximal spacing information, and can utilize that information to dynamically adjust its own cleaning routine, and/or it can utilize that information to cause another oral care device to dynamically adjust its cleaning routine. For example, a flossing device may obtain interproximal spacing information and adjust one or more parameters of the flossing, such as spray velocity, amount, or mixture, and can communicate that information to a toothbrush, or application such that the user—or the device itself—will be directed to adapt a subsequent tooth brushing session. Accordingly, the flossing device and the toothbrush, or application are in wired or wireless communication that allows them to communicate information such as interproximal spacing information in one or both directions. This provides an enhanced cleaning protocol for the user without requiring multiple devices configured to obtain interproximal spacing information.

According to an embodiment, oral care device 10 dynamically adapts to obtained or received interproximal spacing information by, for example, directing the user to do extra rinses, to use a specific cleaning liquid, to use a specific function head, to use a specific size or shape of an function head, or any of a variety of other responses. At step 860 of the method, the system may direct the user to order specific cleaning products based on obtained or received interproximal spacing information, or may automatically order or request these products directly via communication with a network and shopping function or application. The system may provide suggestions about where and when to buy such products, such as a location feature for local stores.

At optional step 870 of the method, the oral care device or system can provide real-time and/or stored feedback data to a user or to a remote system. For example, the system can transmit real-time feedback data to a computer via a wired or wireless network connection. As another example, the system can transmit stored feedback data to a computer via a wired or wireless network connection. In addition to these feedback mechanisms, many other mechanisms are possible. For example, the feedback can combine interproximal spacing information, cleaning time and efficacy, and other information into a display, report, or even a single value, among other types of feedback.

At optional step 880 of the method, the generated feedback is communicated to a user, a device, and/or another individual. The feedback can be real-time feedback, or can be feedback regarding one or more historical sessions. According to an embodiment, the feedback is provided to the user via a smartphone, a computer program, a base station, a remote software service, or via other means. According to another embodiment, the feedback is provided directly to a healthcare professional such as a dentist or dental hygienist. For example, information about one or more scanning or cleaning sessions can be stored and transmitted to a healthcare professional automatically or upon request. According to an embodiment, the information can be stored on the user's smartphone and then brought to the dentist's office during a visit, where the information is automatically uploaded via a Bluetooth connection. The dentist can then review the feedback and utilize that information during care.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more"

of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for adjusting a user's oral care routine by an oral care device based on interproximal spacing, the method comprising the steps of:

measuring, using the oral care device, a size of one or more interproximal spaces within a user's mouth; and dynamically adjusting a volume of fluid delivered to the one or more interproximal spaces by increasing or decreasing the volume of fluid based on the measured size of the one or more interproximal spaces.

2. The method of claim 1, wherein said measuring step comprises a mechanical measurement of the interproximal space.

3. The method of claim 1, wherein said oral care device further comprises a sensor configured to measure the size of the interproximal space.

4. The method of claim 1, wherein said measuring step comprises receiving, by the oral care device, the size of an interproximal space in the user's mouth.

5. The method of claim 1, wherein the dynamic adjustment occurs at the interproximal space.

6. The method of claim 1, wherein adjusting the volume of fluid comprises adjusting a width or number of sprays emitted from the oral care device.

7. The method of claim 1, wherein said oral care device comprises a plurality of tooth-engaging parts biased away from a fixed part, wherein the plurality of tooth-engaging parts are configured to mechanically respond to the interproximal space by moving towards the fixed part.

8. An oral care device configured to automatically and dynamically adjust a cleaning parameter of the oral care device based on a size of one or more interproximal spaces within a user's mouth, the device comprising a sensing and actuation mechanism configured to: (i) measure the size of an interproximal space in the user's mouth; and (ii) automatically adjust, based on the measured size of the one or more interproximal spaces, a volume of fluid delivered to the one or more interproximal spaces of the oral care device, by increasing or decreasing the volume of fluid.

9. The oral care device of claim 8, further comprising a controller configured to analyze the size of the interproximal space in the user's mouth, wherein said automatic adjustment is based at least in part on the analysis.

10. The oral care device of claim 8, wherein said sensing and actuation mechanism comprises a mechanical element configured to directly measure the interproximal space.

11. The oral care device of claim 8, wherein said sensing and actuation mechanism comprises a sensor configured to measure the size of the interproximal space.

12. The oral care device of claim 8, wherein the dynamic adjustment occurs at the interproximal space.

13. The oral care device of claim 8, wherein adjusting the volume of fluid comprises adjusting a width or number of sprays emitted from the oral care device.

14. The oral care device of claim 8, wherein said oral care device comprises a plurality of tooth-engaging parts biased away from a fixed part, wherein the plurality of tooth-engaging parts are configured to mechanically respond to the interproximal space by moving towards the fixed part.

* * * * *